US00PP23316P2

(12) United States Plant Patent
Pan

(10) Patent No.: US PP23,316 P2
(45) Date of Patent: Jan. 8, 2013

(54) ***LANTANA* PLANT NAMED 'LANZ0003'**

(50) Latin Name: ***Lantana camara* L.**
Varietal Denomination: LANZ0003

(75) Inventor: Shifeng Pan, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 13/317,060

(22) Filed: Oct. 7, 2011

(51) Int. Cl.
*A01H 5/00* (2006.01)

(52) U.S. Cl. ..... Plt./227

(58) Field of Classification Search ..... Plt./227
See application file for complete search history.

*Primary Examiner* — Annette Para
(74) *Attorney, Agent, or Firm* — Joshua L. Price

(57) ABSTRACT

A new *Lantana* plant named 'LANZ0003' particularly distinguished by the large sized, two-toned yellow flowers, with good floriferousness as a result of limited seed set, and a relatively compact habit with medium green foliage.

1 Drawing Sheet

Latin name of the genus and species of the plant claimed: *Lantana camara* L.

Varietal denomination: 'LANZ0003'.

BACKGROUND OF THE NEW PLANT

The present invention comprises a new *Lantana*, botanically known as *Lantana camara* L., and hereinafter referred to by the variety name 'LANZ0003'.

'LANZ0003' is a product of a planned breeding program. The new cultivar has large sized, two-toned yellow flowers, with good floriferousness as a result of limited seed set, and a relatively compact habit with medium green foliage.

'LANZ0003' originates from a hybridization made in July 2007 in a controlled breeding program in Gilroy, Calif., USA. The female parent was unpatented, proprietary plant identified as 'G307-1' with a peach color, a larger flower size, more floriferousness and is about four days later to flower.

The male parent of 'LANZ0003' was identified as 'G292-1', an unpatented, proprietary plant with peach color, larger flowers, and a tighter compact habit. The resultant seed was sown in December 2007.

'LANZ0003' was selected as one flowering plant within the progeny of the stated cross in April 2008 in a controlled environment in Gilroy, Calif.

The first act of asexual reproduction of 'LANZ0003' was accomplished when vegetative cuttings were propagated from the initial selection in December 2008 in a controlled environment in Gilroy, Calif.

BRIEF SUMMARY OF INVENTION

Horticultural examination of plants grown from cuttings of the plant initiated in December 2008 in Gilroy, Calif., and continuing thereafter, has demonstrated that the combination of characteristics as herein disclosed for 'LANZ0003' are firmly fixed and are retained through successive generations of asexual reproduction.

'LANZ0003' has not been observed under all possible environmental conditions. The phenotype may vary significantly with variations in environment such as temperature, light intensity and day length.

A Plant Breeder's Right for this cultivar was applied for in Canada on Dec. 17, 2010, #10-7126. 'LANZ0003' has not been made publicly available more than one year prior to the filing of this application.

The following traits have been repeatedly observed and are determined to be basic characteristics of the new variety. The combination of these characteristics distinguishes this *Lantana* as a new and distinct variety.

BRIEF DESCRIPTION OF THE PHOTOGRAPHS

The accompanying photographic drawing shows typical flower and foliage characteristics of 'LANZ0003' with colors being as true as possible with an illustration of this type. The photographic drawing shows a flowering plant of the new variety, and a close-up of the flowers.

DETAILED BOTANICAL DESCRIPTION

The plant descriptions, measurements and aforementioned photographs were taken in Gilroy, Calif. in April 2011 in a greenhouse. These plants were growing in 4.5 inch pots in a trial setting. The plants were about 12 weeks of age and were grown with several early sprays of Paclobutrazol, a plant growth regular.

Color Chart used: Royal Horticultural Society Colour Chart (R.H.S.) 2001

TABLE 1

DIFFERENCES BETWEEN THE NEW VARIETY 'LANZ0003' AND A SIMILAR VARIETY

| | 'LANZ0003' | 'Balandimpea' (U.S. Plant Pat. No. 19,358) |
|---|---|---|
| Flower size: | Larger | Smaller |
| Quantity of flowers: | More floriferousness | Less floriferousness |
| Plant habit: | More compact | Less compact |

Plant:

*Form, growth and habit.*—Relatively compact and bushy, well-branched with apical pinching enhancing the number of branches and results in a tighter plant habit.

*Plant height.*—13.0-16.0 cm.
*Plant height* (*inflorescence included*).—16.0-17.0 cm.
*Plant width.*—35.0-40.0 cm.

Foliage:
*Type*.—Opposite.
*Immature, leaf color, upper surface*.—RHS 137A but a little deeper.
*Lower surface*.—Closest to RHS 137C.
*Mature, leaf color, upper surface*.—RHS 137A but a little deeper.
*Lower surface*.—Closest to RHS 137C.
*Length.*—5.6-6.1 cm.
*Width.*—3.7-3.8 cm.
*Shape*.—Ovate.
*Base shape*.—Attenuate.
*Apex shape*.—Acute.
*Margin*.—Serrulate.
*Texture, upper*.—Hirsute.
*Lower surface*.—Hirsute.
*Color of veins, upper surface*.—RHS 144A.
*Color of veins, lower surface*.—RHS 144B.
*Petioles color*.—RHS 144A.
*Petioles length.*—1.0-1.8 cm.
*Diameter of petiole.*—0.2 cm.
*Texture*.—Hirsute, glandular hairs.

Stem:
*Quantity of main stems.*—4-6.
*Color of stem.*—RHS 144A.
*Length of stem.*—2.0-15.0 cm.
*Diameter.*—0.2-0.3 cm.
*Length of internodes.*—0.5-1.8 cm.
*Texture*.—Hirsute; glandular hairs.

Inflorescence:
*Type*.—Umbel like, flattened semi-sphere the florets are sessile on an ovate receptacle.
*Blooming habit*.—Flowers continuously from spring through fall.
*Number of open flowers per inflorescence*.—About 24 with numerous buds.
*Quantity of inflorescences per plant*.—About 13-15.
*Lastingness of individual blooms on the plant*.—About 4 weeks (depending on temperatures).
*Fragrance*.—Slightly spicy.
*Umbel horizontal diameter*.—About 5.0 cm.
*Umbel depth*.—About 2.5 cm.
*Peduncle color*.—Between RHS 144A and RHS 144B.
*Length of peduncle.*—6.5-7.5 cm.
*Peduncle diameter.*—0.15 cm.
*Texture*.—Hirsute; glandular hairs.

Corolla:
*Floret form*.—Salver-shaped to shallow cup-shaped and zygomorphic, with a relatively long tube at the base. Each flower subtended by a single bract.
*Floret horizontal diameter.*—1.0-1.1 cm.
*Floret depth.*—1.6 cm.
*Immature, color of petals, upper surface*.—RHS 6A with RHS 4c margins.
*Lower surface*.—RHS 4D.
*Mature, color petals, upper surface*.—RHS 6B with RHS 4C margins.
*Lower surface*.—RHS 4D.
*Petal length.*—0.4-0.6 cm.
*Petal diameter.*—0.4-0.6 cm.
*Apex*.—Mucronulate.
*Margin*.—Entire.
*Shape*.—Obovate.
*Degree of lobation*.—Moderate.
*Texture, upper surface*.—Papillose.
*Lower surface*.—Papillose.
*Corolla tube, color, outer surface*.—RHS 4C with overlaid hints of RHS 3C.
*Color, inner surface*.—RHS 8C to RHS 8D.
*Corolla tube length.*—1.2 cm.
*Diameter* (*at opening*).—0.2 cm.
*Corolla tube texture, outer surface*.—Pubescent.
*Inner surface*.—Glabrous.

Bud (just before opening):
*Color*.—RHS 4C.
*Length.*—1.3-1.5 cm.
*Width.*—0.3.
*Shape*.—Tubular.

Bract:
*Color*.—RHS 137D.
*Length.*—0.5 cm.
*Diameter.*—0.2 cm.
*Texture, upper surface*.—Glabrous.
*Lower surface*.—Glandular hairs.

Calyx:
*Number of sepals.*—5, fused sepals forming a short tube around the base of each floret.
*Color of sepals*.—RHS 144D.
*Length of sepals.*—0.2-0.3 cm.
*Width of sepals.*—0.2 cm.
*Apex shape*.—Acute.
*Apex margins*.—Slightly fringed.
*Texture, outer surface*.—Pubescent.
*Inner surface*.—Glabrous.

Reproductive organs:
*Pistil.*—1.
*Length.*—0.2-0.3 cm.
*Style color*.—RHS 4D.
*Style length.*—0.2 cm.
*Stigma color*.—RHS N144A.
*Stamens.*—4.
*Color of filaments*.—RHS 1D but lighter.
*Length filaments.*—0.4 cm.
*Anther color*.—RHS 199C.
*Length of anthers.*—0.1 cm.
*Pollen amount*.—Sparse.
*Color of pollen*.—Not observed on this hybrid.

Fertility/seed set: Fertility/seed set has not observed on this hybrid.

Disease/pest resistance: Disease/pest resistance has not been observed on this hybrid.

What is claimed is:

1. A new and distinct variety of *Lantana* plant named 'LANZ0003' substantially as illustrated and described herein.

* * * * *

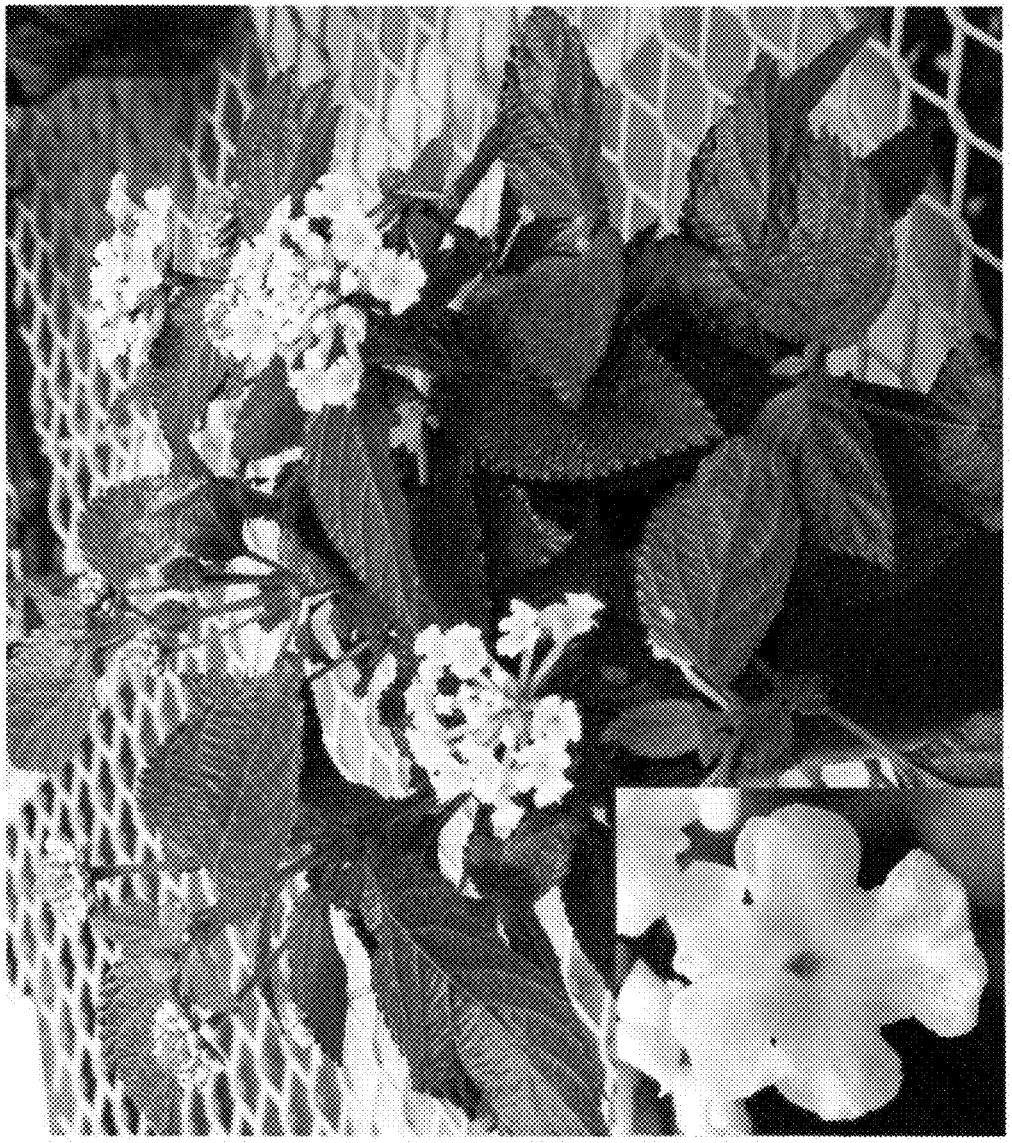

UNITED STATES PATENT AND TRADEMARK OFFICE

CERTIFICATE OF CORRECTION

PATENT NO. : PP23,316 P2
APPLICATION NO. : 13/317060
DATED : January 8, 2013
INVENTOR(S) : Pan It is certified that error appears in the above-identified patent and that said Letters Patent is hereby corrected as shown below:

At column 3, line 57, delete “4c” and insert therefor --4C--

At column 4, line 20, delete “0.3” and insert therefor --0.3 cm--

Signed and Sealed this
Nineteenth Day of February, 2013

Teresa Stanek Rea
*Acting Director of the United States Patent and Trademark Office*